United States Patent
De Marchi et al.

(10) Patent No.: US 10,473,629 B2
(45) Date of Patent: Nov. 12, 2019

(54) PIEZOELECTRIC SENSOR, SYSTEM AND METHOD FOR MONITORING THE INTEGRITY OF STRUCTURES

(71) Applicant: ALMA MATER STUDIORUM—UNIVERSITA DI BOLOGNA, Bologna (IT)

(72) Inventors: Luca De Marchi, Bologna (IT); Nicola Testoni, Casalecchio di Reno (IT); Paolo Francia, Zola Predosa (IT); Guido Masetti, Casalecchio di Reno (IT); Alessandro Marzani, Bologna (IT)

(73) Assignee: ALMA MATER STUDIORUM—UNIVERSITÀ DI BOLOGNA, Bologna (IT)

( * ) Notice: Subject to any disclaimer, the term of this patent is extended or adjusted under 35 U.S.C. 154(b) by 334 days.

(21) Appl. No.: 15/510,081

(22) PCT Filed: Sep. 4, 2015

(86) PCT No.: PCT/IB2015/056755
§ 371 (c)(1),
(2) Date: Mar. 9, 2017

(87) PCT Pub. No.: WO2016/038517
PCT Pub. Date: Mar. 17, 2016

(65) Prior Publication Data
US 2017/0248556 A1    Aug. 31, 2017

(30) Foreign Application Priority Data
Sep. 11, 2014  (IT) .............. MI2014A1571

(51) Int. Cl.
*G01N 29/50* (2006.01)
*G01N 29/07* (2006.01)
(Continued)

(52) U.S. Cl.
CPC ............. *G01N 29/50* (2013.01); *G01H 11/08* (2013.01); *G01N 29/041* (2013.01); *G01N 29/07* (2013.01);
(Continued)

(58) Field of Classification Search
CPC ........... G01H 11/08; G01N 2291/0231; G01N 2291/0258; G01N 2291/106;
(Continued)

(56) References Cited

U.S. PATENT DOCUMENTS

| 2005/0134150 A1* | 6/2005 | Kikushima | ........... H01L 41/053 310/344 |
| 2009/0188319 A1* | 7/2009 | Giurgiutiu | ............ B06B 1/0692 73/594 |
| 2010/0329932 A1* | 12/2010 | Yorita | .................. G01N 29/022 422/82.01 |

* cited by examiner

*Primary Examiner* — John H Le
(74) *Attorney, Agent, or Firm* — Patshegen IP LLC; Moshe Pinchas (57) ABSTRACT

The present invention relates to a piezoelectric sensor (1,100) comprising a piezoelectric material (10) interposed between a first (11) and a second (12) electric contact element. The first electric contact element (11) comprises at least two sensing areas (110, 111) spatially separated along a sensing direction. It also describes a sensor node that includes the piezoelectric sensor, a system and a method for monitoring the integrity of a structure using said piezoelectric sensor.

23 Claims, 11 Drawing Sheets

(51) Int. Cl.
    *G01N 29/24*    (2006.01)
    *G01N 29/04*    (2006.01)
    *G01H 11/08*    (2006.01)
(52) U.S. Cl.
    CPC ..... *G01N 29/2437* (2013.01); *G01N 29/2475* (2013.01); *G01N 2291/0231* (2013.01); *G01N 2291/0258* (2013.01); *G01N 2291/106* (2013.01)
(58) Field of Classification Search
    CPC .. G01N 29/041; G01N 29/07; G01N 29/2437; G01N 29/2475; G01N 29/50
    USPC ...... 702/34, 35, 56, 92, 93, 127, 27; 73/594, 73/587; 340/350; 310/311, 344; 422/82.01
    See application file for complete search history.

PIEZOELECTRIC SENSOR, SYSTEM AND METHOD FOR MONITORING THE INTEGRITY OF STRUCTURES

TECHNICAL FIELD

The present invention relates to the field of piezoelectric sensors and methods of monitoring the structural integrity of structures, in particular structures with a prevailing surface development (plates or panels, smooth or corrugated), whether isotropic or made from composite materials. The invention relates, in particular, to a sensor according to the preamble of claim 1, to a system and a method that use said sensor in order to localize and quantify any impacts within the aforesaid structures.

PRIOR ART

Today many systems for monitoring the integrity of structures that are called SHM ("Structural Health Monitoring") systems are known.

Some of these systems have in common the use of a network of sensors designed to detect impacts and/or anomalies in the monitored structures, and to transmit these measurements to a data acquisition system (DAQ).

Depending on the structural type of the structure to be monitored and the material it is made of, different monitoring systems are used.

In the case of thin structures in composite materials, widely used in the aviation and aerospace fields, monitoring systems based on the diagnostic method of bulk or guided elastic waves, also referred to hereinafter as elastic waves, are considered to be among the most promising. These monitoring systems use a network (array) of (small and light) piezoelectric transducers, glued to or incorporated into the structure (generally in the superficial layers of the structure) designed to generate and receive elastic waves. The network of sensors is controlled by an appropriate data acquisition system (DAQ). Elastic waves acquired by the sensors in the form of time responses are subsequently treated with signal processing instruments in order to detect possible impacts and/or damage to the structure, as well as to locate their position.

As promising as they may be, to date, the potential of the monitoring systems based on elastic waves for the detection of impacts for structures of composite material are limited by some physical aspects related to the nature of the material itself as well as by various constraints inherent in the current technologies. Composite materials, in fact, diminish the mechanical energy of elastic waves much faster than metals. Therefore the propagation of waves in a composite structure is reduced compared to that in a metal structure of the same shape and thickness. Furthermore, since in composite structures the propagation is anisotropic, i.e. dependent on the direction of propagation, many of the diagnostic methods available are inadequate.

Consequently the prior art in the detection of impacts in composite structures by means of elastic waves generally consists of monitoring systems characterized by:

- dense sensor networks (a large number of sensors per unit area);
- sophisticated signal processing techniques that require rather powerful computing platforms;
- high complexity of the wiring between the sensors and the processing units.

The SHM systems currently used for the monitoring of structures with elastic waves are therefore characterized by elevated overall dimensions, weight, power consumption, and maintenance costs. Examples of systems which suffer from one or more of these problems are known from the patent applications US20070114422, US20070118335, US20130343424, EP2078943A2 and from the U.S. Pat. No. 8,234,924.

Among the SHM systems that exploit elastic waves, there are also systems (such as those known from EP2078943A2, EP2485026A1, U.S. Pat. Nos. 7,430,911, 8,234,924), which are limited by a lack of consolidated project methodologies for their application to composite materials subjected to temperature variations, humidity, pressure, etc., conditions that often occur in composite structures used in the aeronautical and aerospace sectors.

PURPOSE AND SUMMARY OF THE INVENTION

The purpose of the present invention is to overcome the limitations of the SHM systems known from the prior art.

In particular, a purpose of the present invention is to present a piezoelectric sensor whose use for monitoring the integrity of a structure allows the problems of the prior art to be overcome.

Another purpose of the present invention is to present a system for monitoring the integrity of a structure with a low weight.

Yet another purpose of this invention is to present a system for monitoring the integrity of a structure that requires low energy consumption.

These and other purposes of the present invention are achieved by means of a piezoelectric sensor, a system and a method for the detection of impacts in a structure, which incorporate the features of the attached claims.

The idea underlying the present invention envisages the realization of a piezoelectric sensor comprising a piezoelectric material interposed between a first and a second electric contact element. At least one of these electric contacts, for example the first, comprises at least two spatially separated sensing areas.

In particular, the two spatially separated sensing areas have a shape such that upon a variation of the sensing direction of the sensor (depending on the direction of arrival of the wave), the distance between the points where the wave impacts the two sensing areas also varies. In other words, the two spatially separated sensing areas have a shape such that their separation and extension vary when any changes in the sensing direction taken into consideration occur.

This solution offers the advantage that when an elastic wave affects and stimulates the piezoelectric sensor, it responds by generating an electrical signal with characteristics that depend both on the energy of the wave, and on the direction of origin of the wave. It is thus possible to process the signal generated by such a sensor in order to derive therefrom the energy and the direction of origin of the elastic wave.

Working, therefore, with a plurality of sensors placed in contact with or incorporated into the structure, such as the skin of the fuselage of an airplane, it is possible to determine the point and the energy of the impact that caused the elastic wave detected by the piezoelectric sensors.

In one embodiment, the two sensing areas are electrically connected, so that the direction of origin of the elastic wave can be determined by calculating the autocorrelation signal of the signal generated by the piezoelectric sensor, and extracting the second peak of the autocorrelation signal.

Alternatively, the two sensing areas are electrically insulated and constitute two separate electrodes, each equipped with a respective output terminal connected to a respective sensing area. In this case, the direction of origin of the elastic wave can be determined by calculating the cross-correlation signal of the two signals generated by the piezoelectric sensor, and extracting the maximum peak of the cross-correlation signal.

In one particularly advantageous embodiment, which allows the sensing of elastic waves in a range of 90°, one of the two sensing areas has a circular shape and the second has the shape of a segment of an Archimedean spiral or of a logarithmic spiral.

Another subject of the present invention is a sensor node, i.e. a device comprising a piezoelectric sensor of the type indicated above and described further below, and a processing unit designed to digitize an electrical signal generated by the piezoelectric sensor in response to the detection of an elastic wave and transmit the digitized signal to a remote device.

A sensor node of this type is suitable for use in a system for monitoring the integrity of a structure where a central system collects the data transmitted by the various sensor nodes and determines the position and the energy of the impact that caused the elastic wave detected by the sensor network.

In one embodiment, the processing unit is designed to calculate the direction of origin and/or the energy of the elastic wave and to transmit said data to a remote device. In this embodiment, the sensor node is complete and able to autonomously process the signal generated by the sensor node. Alternatively, however, it is possible to delegate the processing of the digitized signal to a remote device. This way less complex sensor nodes and lower power consumption can be achieved.

In one embodiment, the sensor node further comprises means for receiving and/or transmitting data over optical fibre. This allows connection of the sensor node to another device by means of optical fibre, which in some applications, for example where electro-magnetic interferences are a problem, is preferable to a copper connection.

In one embodiment, the sensor node also includes an area of memory for temporarily storing data received on a data input. This allows the realization of sensor networks that are particularly efficient in terms of weight. The sensor nodes of this type, in fact, can be connected to one another and not necessarily to a central element of a network in a star configuration. This reduces the number and/or the length of the connections between nodes, thus achieving an overall reduction of the system.

Further subjects of the present invention are a system and a method for monitoring the integrity of a structure using a piezoelectric sensor or a sensor node of the type mentioned above and further described in the following description.

BRIEF DESCRIPTION OF THE DRAWINGS

The invention will be described hereinafter with reference to non-limiting examples, provided by way of explanatory and non-limiting examples in the appended drawings. These drawings illustrate different aspects and embodiments of the present invention and, where appropriate, reference numerals illustrating structures, components, materials and/or similar elements in different figures are indicated by similar reference numerals.

DETAILED DESCRIPTION OF THE INVENTION

While the invention is susceptible to various modifications and alternative constructions, some preferred related embodiments are shown in the drawings and will be described below in detail. It should be understood, however, that there is no intention to limit the invention to the specific illustrated embodiments, but, on the contrary, the invention intends to cover all the modifications, alternative constructions, and equivalents as fall within the scope of the invention as defined in the claims.

The use of "for example", "etc.", "or" indicates non-exclusive alternatives without limitation unless otherwise indicated. The use of "includes" means "includes, but is not limited to" unless otherwise indicated.

Use of the term "gain" for a transfer function is meant to indicate the ratio between the amplitudes of the output and input signals; a gain can therefore be greater than 1 (amplification) or lower than one (attenuation).

Use of the term "sensing direction" is meant to indicate any direction along which the piezoelectric sensor is able to detect the arrival of an elastic wave. The sensing direction may coincide with or be different from the direction of origin of the wavefront, given that a wavefront may impact the piezoelectric sensor even if it comes from a direction of origin that is external to the sensing lobe of the piezoelectric sensor.

Figure 1:
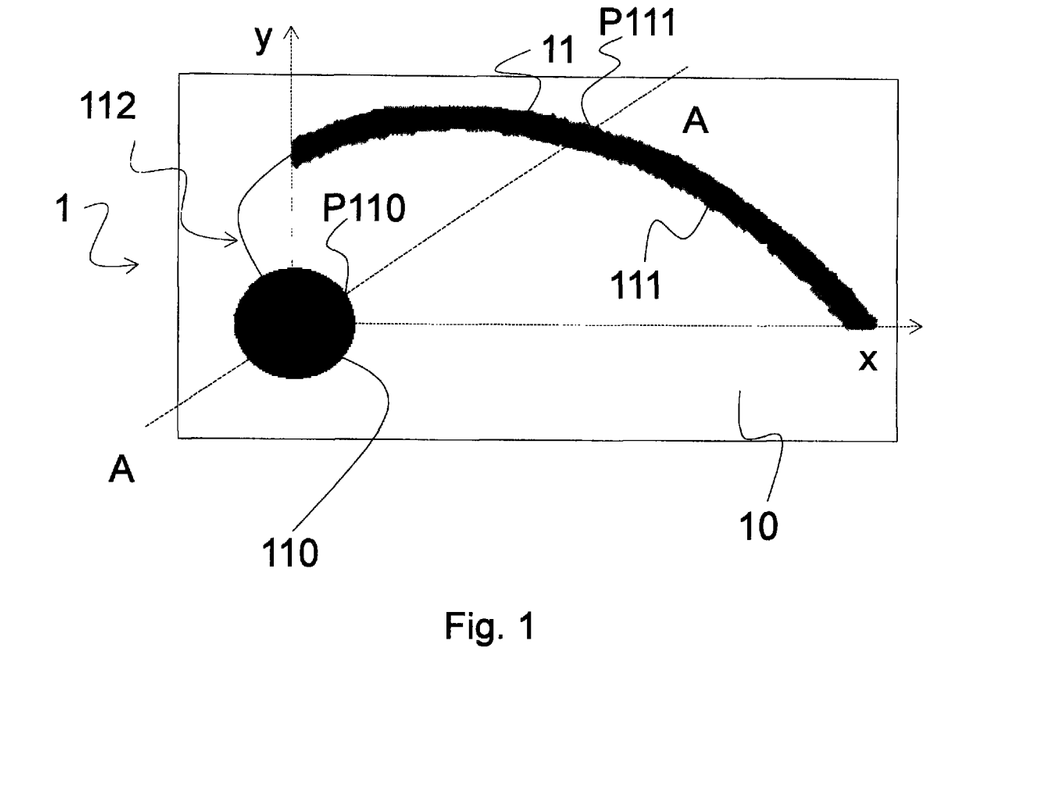
FIG. 1 shows a top view of a piezoelectric sensor according to one embodiment of the present invention.

FIG. 1 shows a top view of a piezoelectric sensor 1 that is particularly suitable for use in networks for monitoring the integrity of structures.

Figure 2:
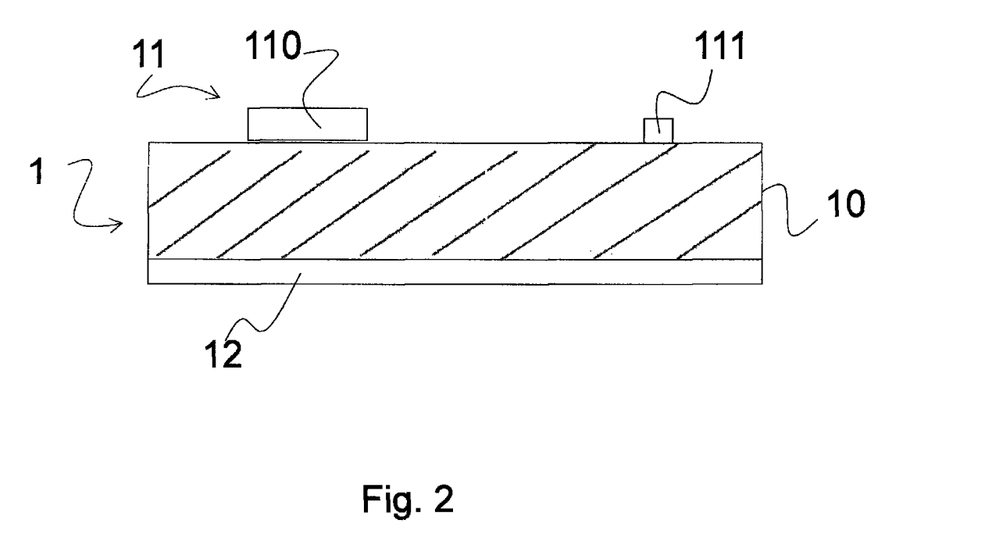
FIG. 2 shows a sectional view of the sensor in FIG. 1.

The sensor 1, whose section along the axis AA is shown in FIG. 2, comprises a substrate 10 of piezoelectric material and a pair of contact elements 11 and 12, in conductive material, e.g. copper, placed on two opposite surfaces of the substrate 10. In the example in FIG. 1, each contact element is an electrode, however, according to other embodiments described below, each contact element may comprise a number of electrodes.

The electrodes 11 and 12 can be formed in a manner known per se, for example by depositing a metal layer on the piezoelectric substrate 10, and may be of a variable shape and thickness according to the principles better described hereunder.

In the example of FIGS. 1 and 2, the sensor 1 is configured to detect the arrival of guided waves within an angle of 90° identified in FIG. 1 by the axes x and y. The electrode 12, placed along the inferior surface of the substrate 10 is a single piece of constant thickness such as to include the area of the electrode 11, while the electrode 11 includes two sensing areas 110 and 111 spatially separated along a sensing direction AA.

In this embodiment, the two sensing areas 110 and 111 are kept in electrical contact by means of an electrical connection, for example a copper wire, 112, preferably external to the sensing angle of the sensor. The presence of the electrical connection is not essential to the operation of the sensor, but its presence or absence requires a different treatment of the output signal from the sensor.

The sensing areas 110 and 111 have a shape such that their distance (preferably measured between the outermost points, i.e. those that may first encounter an elastic wave propagating through the monitored structure, such as the points P110 and P111 in FIG. 1 along the direction AA) varies when the sensing direction taken into consideration changes. In the example of FIG. 1, this is achieved by means of a first sensing area 110 of circular shape and a second sensing area 111 whose shape corresponds to a portion of a logarithmic spiral. Clearly in order to obtain the angular variation of the distance between the sensing areas of the electrode 11 other forms, such as Archimedean spirals, can be used, and it is possible to vary not only the shape, but also the thickness or the number of conductive areas which constitute the first electrode.

In an embodiment not shown in the Figures, in addition to the electrode 11 the electrode 12 also can have a contoured shape and/or comprise one or more spatially separated sensing areas. The combination of different shapes and thicknesses for the two electrodes 11 and 12 can be used differently to obtain as a result a pair of electrodes formed by sensing areas differently spaced along different sensing directions.

Figure 3:
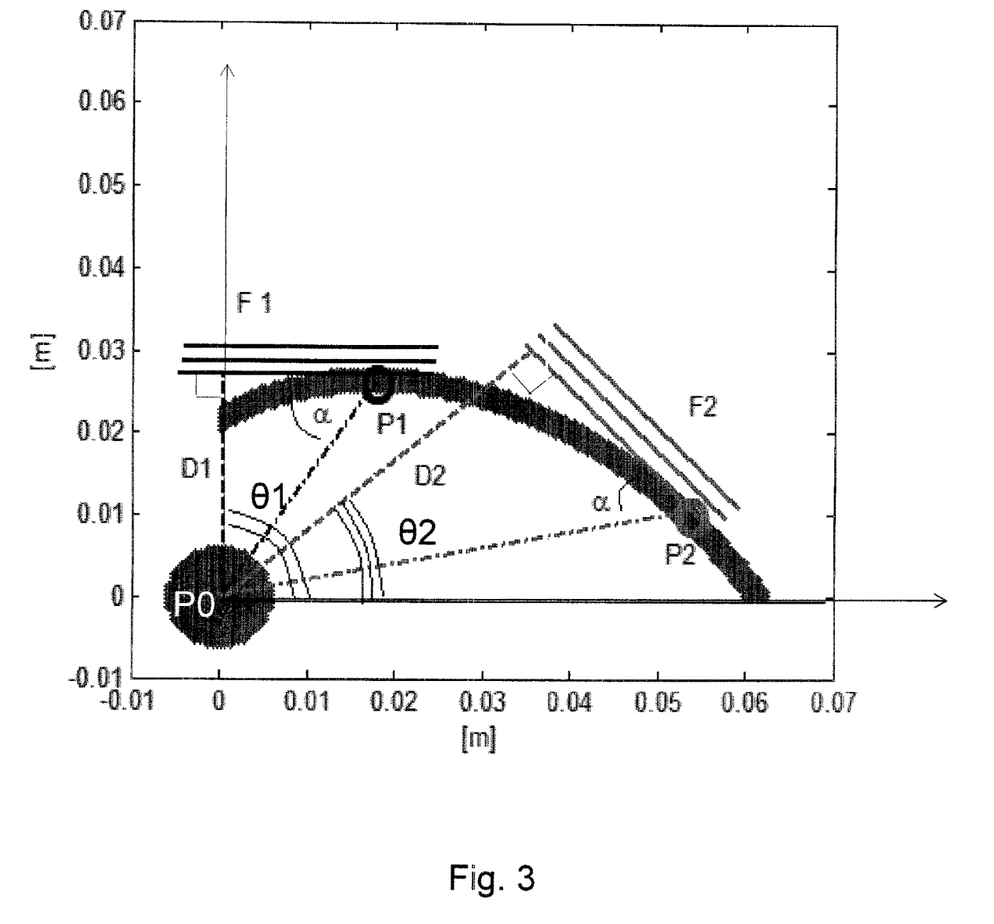
FIG. 3 schematically shows the detection of two wavefronts being detected by the sensor in FIG. 1.

The shape of the sensor 1 permits it to distinguish the angle of arrival of a wavefront, for example due to the impact of an object with the structure monitored by the sensor. FIG. 3 shows two wavefronts, F1 and F2, which impact from different directions of origin (identified respectively by the angles θ1 and θ2) on two different contact points (P1 and P2) on the sensing area 111 of the electrode 11 (events Ea1 and Ea2).

The wavefronts then impact the second sensing area (events Eb1 and Eb2). The time interval (deltaT) between events Ea1 and Ea2 and events Eb1 and Eb2 depends on propagation speed of the elastic wave and on the distances D1 and D2.

In response to each of the two wavefronts, the piezoelectric sensor 1 outputs (i.e. to the electrodes 11 and 12) a different potential difference, according to the direction of origin of the wavefront due to the different deltaT that are determined.

Figure 4:
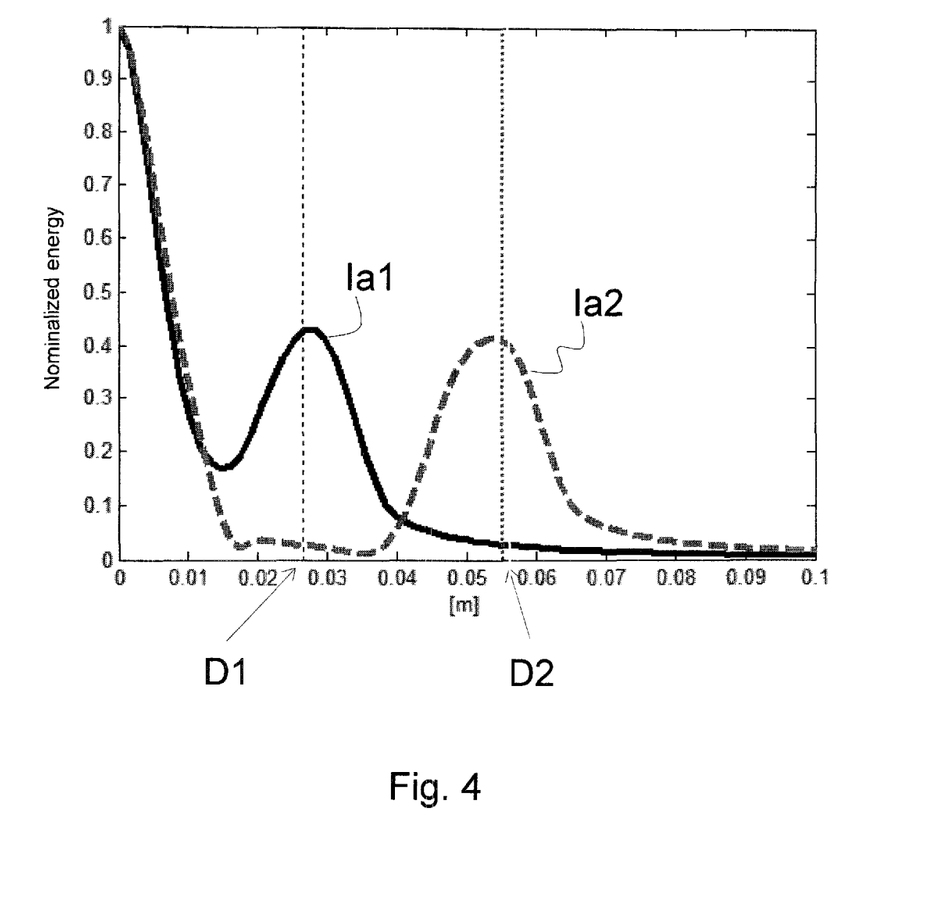
FIG. 4 shows the autocorrelation signals of the signals generated by the sensor in FIG. 1 in response to the waves shown in FIG. 3.

FIG. 4 shows the trend of the autocorrelation envelope (Ia1 and Ia2) of the two signals generated by the wavefronts F1 and F2. As can be seen from FIG. 4, Ia1 and Ia2 both have a main origin peak and a secondary peak (hereinafter also referred to as "2nd peak") whose distance from the main peak depends on the point of impact of the wavefront with the sensing area 111.

In order to distinguish the direction of origin of the wavefront, the output of the sensor 1 is connected to the input of a processing unit 2 which determines the direction of origin of the wavefront.

Figure 5:
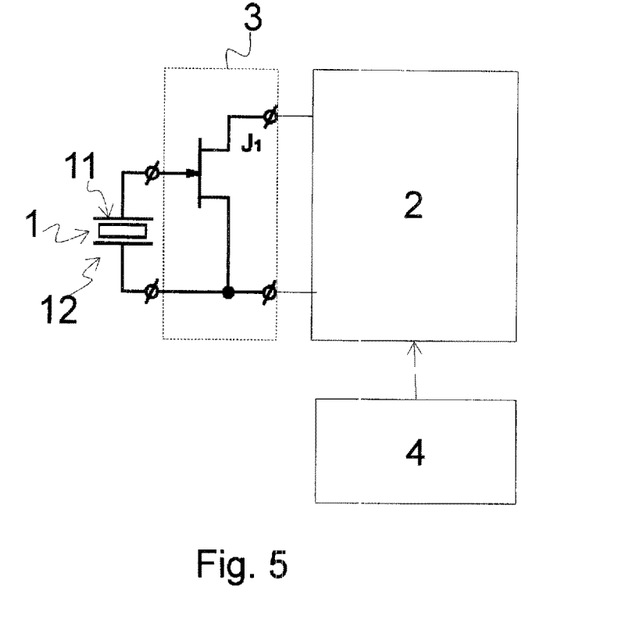
FIG. 5 shows a sensor node that contains the sensor in FIG. 1.

In a preferred embodiment, the piezoelectric sensor 1 is connected to the processing circuit 2 through an impedance matching circuit 3 as shown in FIG. 5.

In the example of FIG. 5, the piezoelectric sensor 1 is connected to a processing unit 2 through an impedance matching circuit, which in this embodiment is constituted by a field-effect transistor, in particular a JFET whose gate and source are connected to the electrodes 11 and 12 of the sensor.

Again with reference to FIG. 5, to supply the processing unit 2 a power supply 4 is provided.

The power supply 4, the processing unit 2, the impedance matching circuit 3 and the piezoelectric sensor 1 are preferably mounted on a same substrate, such as a same PCB (Printed Circuit Board) or more preferably the same substrate of flexible plastic (such as polyamide, PEEK film or transparent conductive polyester). Thus mounted and assembled, these elements constitute a sensor node that can be used as an element of a network for monitoring the integrity of a structure. Alternatively, the various elements of the sensor node can be separated and maintained in electrical connection by means of conventional wiring, for example of twisted copper pairs. The solution of integrating the above elements as much as possible into a single sensor node, however, has the advantage of reducing the weight of the overall structure.

Figure 6:
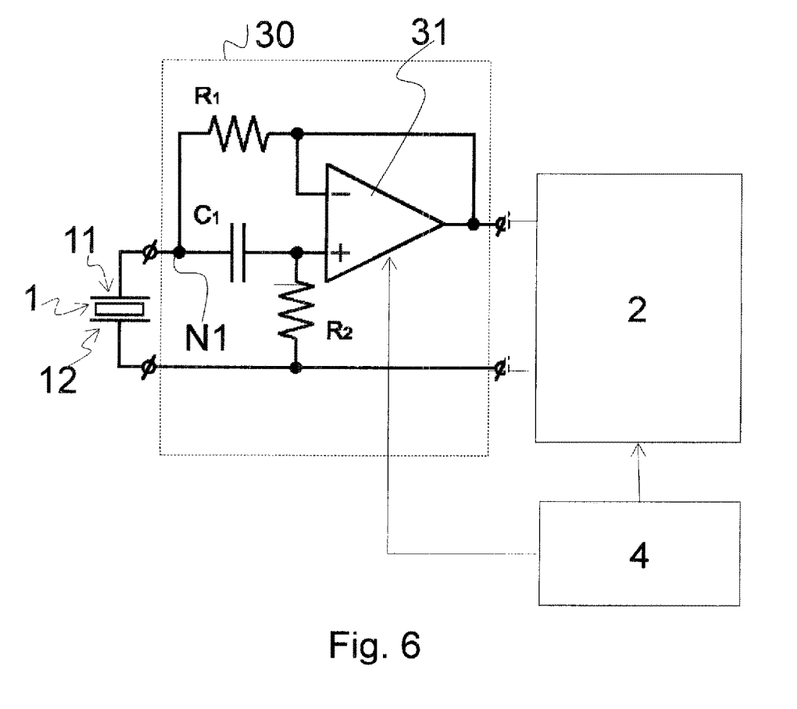
FIG. 6 shows an alternative sensor node to that in FIG. 5.

In one embodiment, shown in FIG. 6, the impedance matching circuit 30 is a filter circuit. The piezoelectric sensor can be represented as a voltage source in series with a capacitor whose capacity depends on the characteristics of the sensor. This capacity of the piezoelectric sensor is connected to the node N1, where the capacitor C1 and the resistor R1 are connected. The entire circuit 30, and the capacity of the piezoelectric sensor, constitute a Bessel filter of the second order, in which the capacitor C1 is connected between the node N1 and the non-inverting input of an operational amplifier 31, the output of which is shorted on the inverting input. One resistor R1 is connected between the node N1 and the inverting input of the operational amplifier 31, while another resistor R2 is connected between the non-inverting input of the operational amplifier 31 and an earth wire which is also connected to the piezoelectric sensor 1.

Knowing the characteristics of the piezoelectric sensor 1 and its equivalent circuit, it is possible to size the resistors R1 and R2 and the capacitor C1 in order to define the bandwidth of the filter. This is particularly advantageous in the case of monitoring the integrity of structures that, during their operation, may be subject to vibrations, for example in the case of monitoring the fuselage of an aeroplane that is subjected to vibrations induced by the engines. Such vibrations are characterized by specific frequencies that corrupt the signal and which must therefore be filtered out. Additionally, the filter itself can be used for an anti-aliasing function before the sampling and the digitizing take place.

The circuit in FIG. 6 foresees connecting to the same earth the electrode 12 of the sensor 1, the impedance matching circuit and the control unit 2. This type of circuit is preferably applied if the sensor is applied on conductive materials, such as aluminium.

Figure 7:
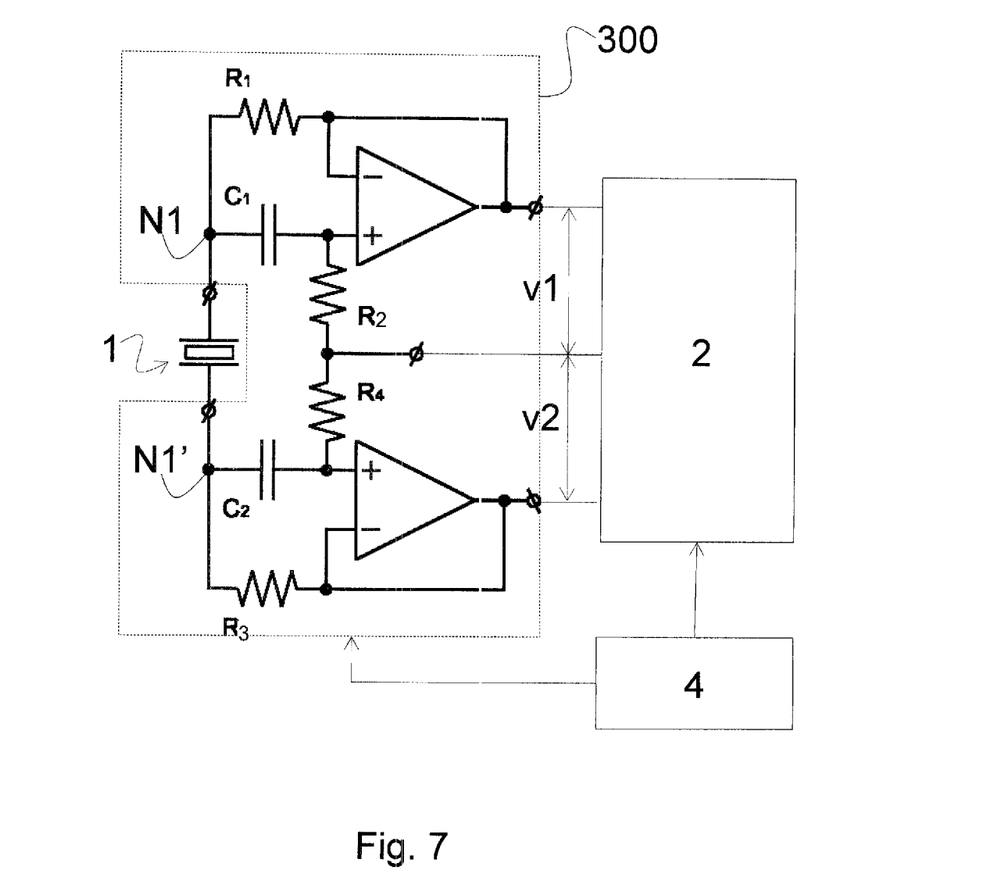
FIG. 7 shows an alternative sensor node to those in FIGS. 5 and 6.

In the event of the sensor being applied on materials that are not good electrical conductors, for example for application on a laminate of carbon fibre (where the resin that aggregates the carbon fibres is an insulator), it is preferable to the use an impedance matching circuit of the type shown in FIG. 7.

In FIG. 7, the impedance matching circuit 300 is a circuit for active adaptation, wherein to each of the two electrodes (11 and 12) of the sensor 1 is connected an impedance matching circuit of the type in FIG. 6, namely a circuit comprising an operational amplifier with an inverting input that is short-circuited at output, a first resistance (R1, R3) connected to the inverting input of the operational amplifier, a capacitor (C1, C2) connected to the first resistor (R1, R3) and to the non-inverting input of the operational amplifier, a second resistor (R2, R4) connected to the non-inverting input of the operational amplifier. The resistors R2 and R4 are connected to each other. As per the example in FIG. 6, in practice there are two second-order Bessel filters which determine the bandwidth of the signal provided at the input to the processing unit 2.

Regardless of the impedance matching circuit used, when a wavefront affects the piezoelectric sensor 1, this generates a potential difference which, as stated above, depends on the direction of origin of the wavefront.

Figure 8:
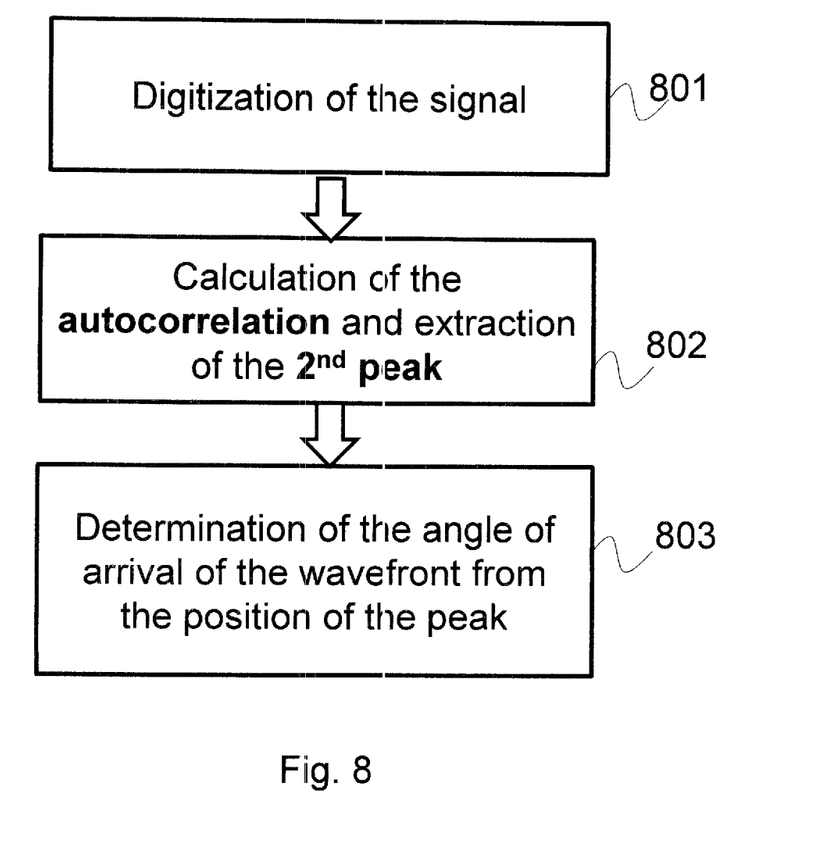
FIG. 8 shows a flow diagram of a method for calculating the direction of origin of an elastic wave detected by a piezoelectric sensor according to the invention.

In order to distinguish the direction of origin of the wavefront, the control unit 2, for example a microprocessor or a microcontroller, executes a method described hereinafter with reference to the flow diagram of FIG. 8.

Firstly, the signal generated by the piezoelectric sensor 1, and possibly filtered by an impedance matching circuit, e.g. of the type illustrated in FIG. 6, is digitized (step 801) by the processing unit 2.

Then the calculation of the autocorrelation envelope of the signal thus processed is made, and the extraction (step 802) of its second peak. This operation can be performed by detecting the position of the maximum of the autocorrelation envelope in the time interval that corresponds to the extreme values of deltaT. These extremes are determined by taking into consideration the minimum and maximum distances between the sensing areas of the sensor and multiplying these distances by the speed of propagation.

On the basis of the position of the second peak (PSP), the processing unit 2 calculates (step 803) the angle of arrival of the wavefront (for example the angles θ1 and θ2 in FIG. 3) detected by the piezoelectric sensor 1. The calculation is made by multiplying PSP by the wave propagation speed in order to obtain the distances that correspond to D1 and D2 in the examples taken into consideration, from which the angular directions can be derived with geometrical considerations related to the shape of the spiral. In particular, in the case of the logarithmic spiral, the fact that the arms of the spiral widen with a geometric progression and that the angle "α" between the radius of the spiral at a point and the tangent to the spiral at that same point is constant, are exploited. In a preferred embodiment, the processing unit is configured to transmit to a remote device a scalar value representative of the direction of impact detected by the sensor 1. Preferably, in addition to this scalar value, the processing unit 2 is configured to transmit to the remote device an identification datum of the sensor node (or sensor 1 if the latter is not integrated into a sensor node as described above) and a temporal indication relating to the moment of receipt of the elastic waves. Even more preferably, the control unit is also configured to transmit to the remote device self-diagnosis data of the control unit or the sensor node in general. While in the above described example each processing unit 2 is configured to calculate the direction of the wavefront, it is, however, possible to provide a sensor node with a simpler configuration that does not calculate the direction of the wavefront, leaving the calculation of the direction of origin of the wavefront to a remote device. In this embodiment, which reduces the computational complexity and therefore the cost and power consumption of the sensor nodes used for monitoring the integrity of a structure, the control unit does no more than digitize the signal generated by the piezoelectric sensor and transmit this signal, for example via a fibre optic connection, to a remote device where the calculation of the direction of origin of the wavefront takes place.

Figure 9:
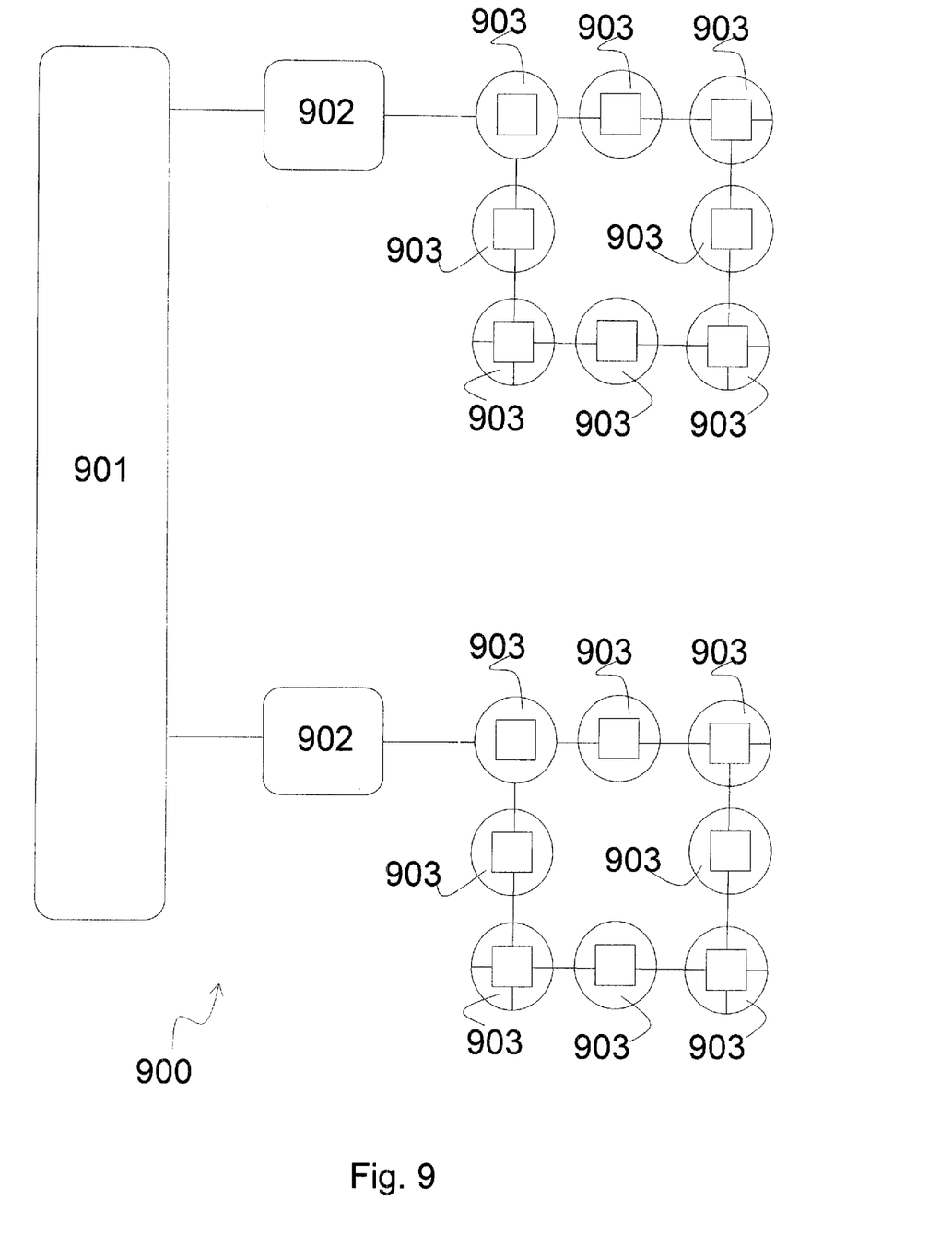
FIG. 9 shows a system for monitoring the integrity of a structure.

FIG. 9 shows an example of a network of sensors for monitoring the integrity of a structure. One or more of the network elements, and preferably all the sensor nodes, are integrated into the structure to be monitored, in particular they are inserted in the surface layers or in the layers immediately underlying the surface layers, of the structure to be monitored.

In the example in FIG. 9, the network 900 includes a central processing system 901, and a plurality of access points 902 that collect the data transmitted by the sensor nodes 903 and transmit them to the central processing system 901. The system in FIG. 9 thus allows the implementation of a method for monitoring the integrity of a structure as described below and illustrated in FIG. 10.

In the example of FIG. 9, each sensor node comprises an input and an output for respectively receiving and transmitting data. Preferably, the transmission is effected by optical fibre, thus each sensor node 903 is provided with suitable devices, such as photodiodes, for receiving and transmitting fibre optic signals.

In the example in FIG. 9, each sensor node 903 reacts to the presence of elastic waves in the monitored structure, for example due to an impact of an object with the monitored structure, by transmitting a digital optical signal (step 1001).

In the preferred embodiment, each sensor node 903 transmits both the digital signal that carries the information on the wave detected, and an identification code of the sensor node.

In the example in FIG. 9, each sensor node 903 transmits these data to the adjacent sensor node 903, which stores them temporarily and transmits them to the adjacent sensor node until they reach the access node 902 which transmits them to the central processing system 901. Other types of connection for the sensor nodes 903 and other systems and protocols for data transmission in the network 900 are however possible.

The central processing system then receives the digitized signals and the identification codes of the sensor nodes 903 of the network 900.

Since in the propagation of elastic waves in structures such as plates and shells there can be dispersion of the elastic wave, within the network 900 suitable forms of compensation of said dispersion can be provided based on known per se algorithms, such as the algorithm described in "A passive monitoring technique based on dispersion compensation to locate impacts in plate-like structures", L De Marchi, A Marzani, N Speciale, E Viola, Smart Materials and Structures 20 (3), 035021. In this paper it is shown how compensation of the dispersion has the effect of generating waveforms for which it is possible to associate propagation distances at time intervals deltaT as in the case of non-dispersive propagation.

Figure 10:
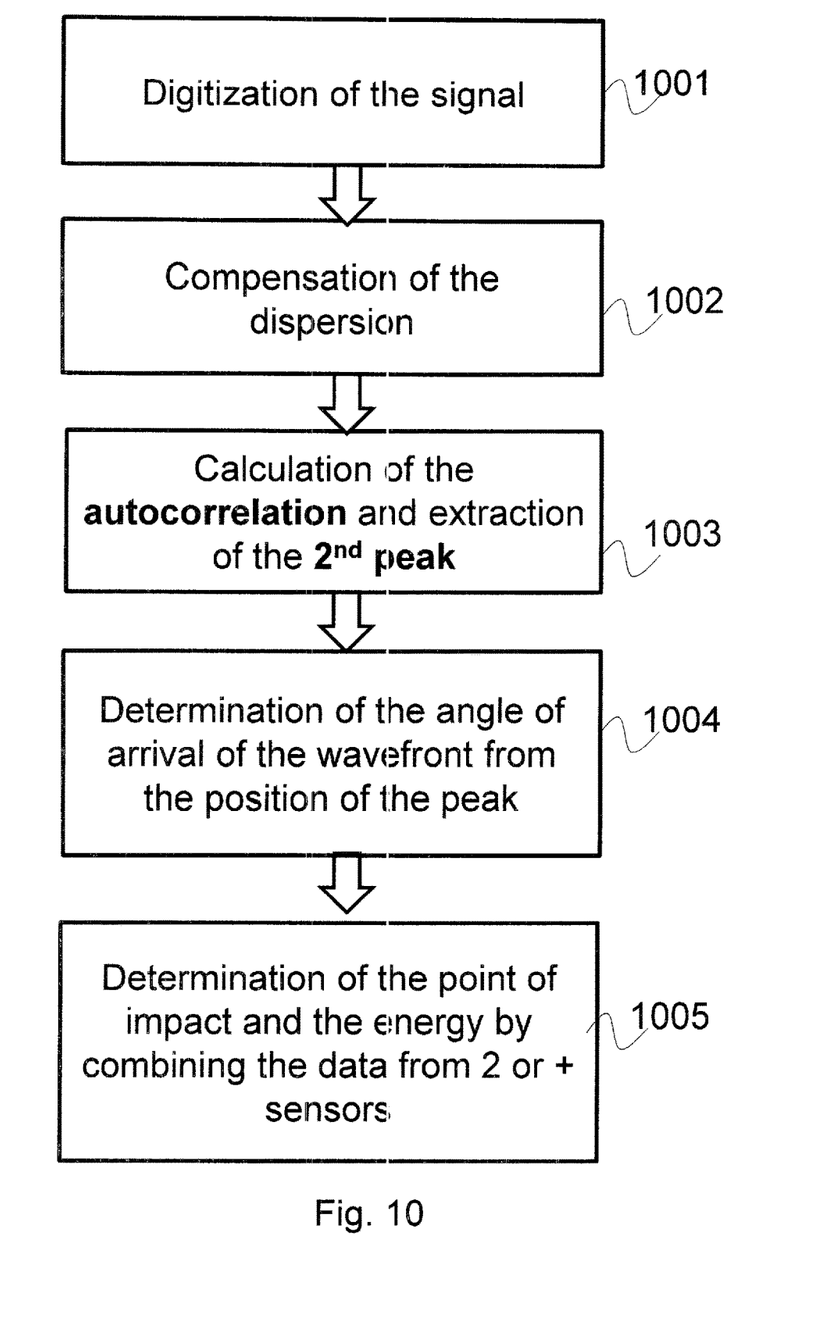
FIG. 10 shows a flow diagram of a method for calculating the position and energy of an elastic wave generated by the impact of an object on the structure.

Such compensation modules (hardware or software) are preferably included in or connected to the central processing system 901, which proceeds therefore to compensate the dispersion of the acquired signal (step 1002) to generate a corresponding compensated signal, however, it is possible to provide dispersion compensation modules inside the sensor nodes also.

The central processing system 901 includes an area of memory that collects information on the various sensor nodes, such as their position in the structure, their shape and the mathematical relation that binds the signal generated by the piezoelectric sensor to the direction of origin of the wavefront. In this way, the central processing system 901 is capable of calculating (step 1003), for every sensor node 903, the autocorrelation of the received digital signal and consequently determine (step 1004) the direction and energy of the wavefront detected by each sensor node 903 of the network 900.

With this information (knowledge of the position of the sensor nodes, the direction and energy of the wavefront detected), the central processing system 901 determines (step 1005) the point of impact and the impact energy from the measurements of the various sensor nodes 903.

There is also the possibility of providing that the sensor node independently determines the direction and energy of the wavefront that activates the piezoelectric sensor 1, as illustrated previously with reference to FIG. 8. In this case the sensor node outputs information regarding its identifier, the direction and the energy of the wavefront detected. The central system then determines the position and energy of the impact by using the information supplied by the various sensor nodes.

In the case of anisotropic materials, the wave generated by an impact with the monitored structure propagates differently in different directions. In order to calculate the point and the energy of an impact, the method of monitoring a structure described above must be partially modified and a preliminary phase in which the structure is characterized is necessary. In this characterization phase, N (with integer N greater than 1) different pre-selected angular directions within the structure are identified and different dispersion curves of different modes of propagation of an elastic wave in the N pre-selected angular directions are calculated.

Figure 11:
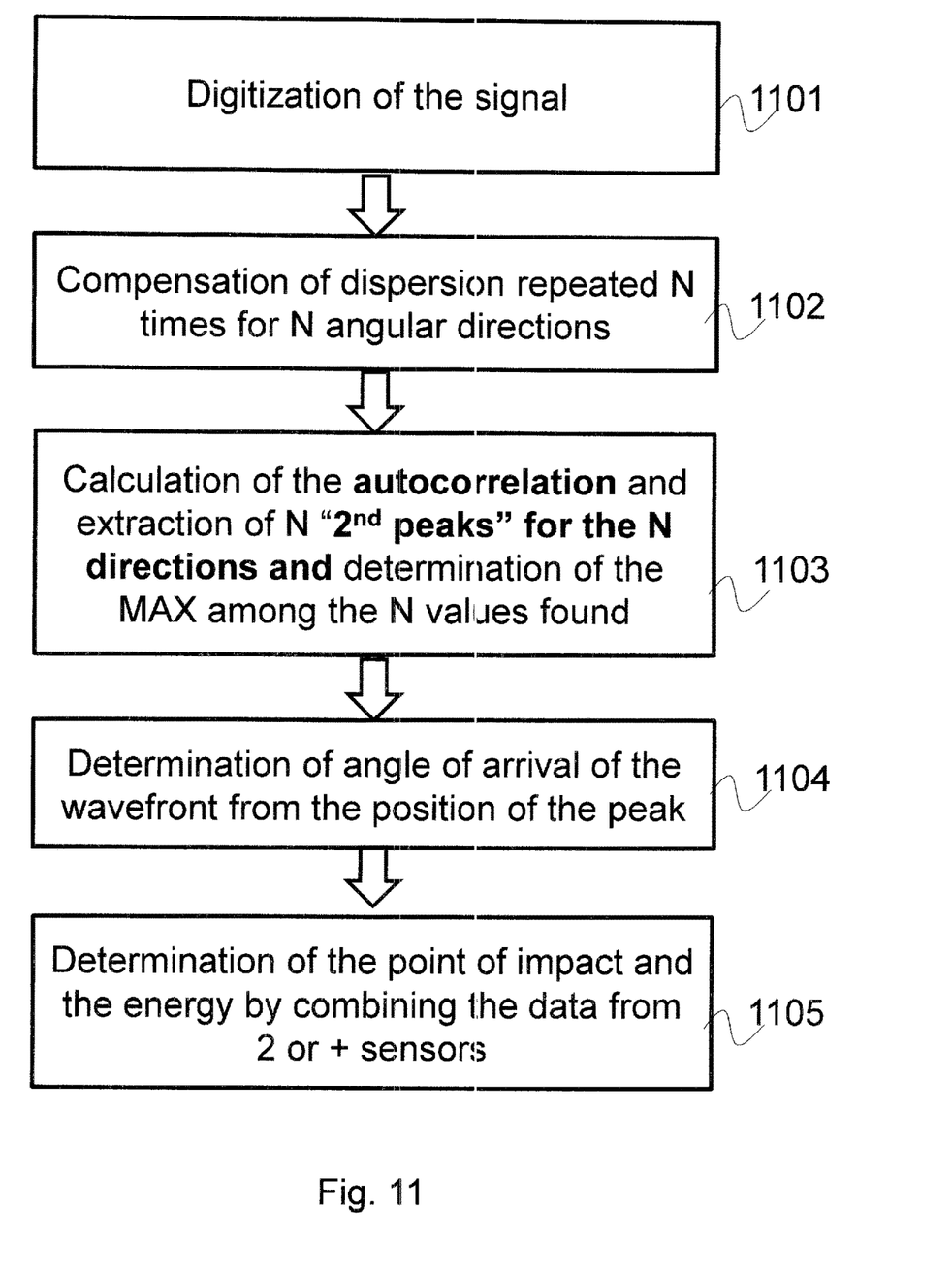
FIG. 11 shows a flow diagram of a method for calculating the position and energy of an elastic wave generated by the impact of an object on the structure in the case of a structure in anisotropic material.

FIG. 11 shows a flow diagram of a method for monitoring the integrity of a structure made of anisotropic materials.

The method involves use of a plurality of sensor nodes connected in a network, for example as shown in FIG. 9.

Each sensor node is configured to digitize (step 1101) the signal generated by the respective on board piezoelectric sensor 1 and transmit, preferably by optical fibre, the signal to an adjacent sensor node.

In the example in FIG. 11, the central processing system receives digital signals with information relating to readings taken by the m sensor nodes 903 of the network 900.

For each of the m received signals, the central processing system performs dispersion compensation (step 1102) repeating same N times for the N different predetermined angular directions selected during the characterization of the structure. At the end of this phase, there will therefore be N compensated signals for each of the m signals transmitted by the m sensor nodes.

Subsequently, for each sensor node, the central processing system (step 1103) calculates the autocorrelation for each of the N compensated signals and extracts N second autocorrelation peaks for the N predetermined angular directions. From among these N second autocorrelation peaks the central system selects the one with the maximum amplitude and, on the basis of this value, determines (step 1104) the direction of origin of the wavefront with respect to each of the m sensor nodes. In this case also, it is possible to provide modules which carry out the dispersion compensation and calculate the direction of origin of the wavefront within the sensor nodes themselves.

Finally, from the position of the m sensor nodes, the direction and the energy of the wavefront detected by each sensor node, the central processing system determines (step 1105) the point of impact and the energy of the impact.

In light of the above it is clear how the piezoelectric sensor, the system and method for monitoring the integrity of a structure described above permit the attainment of the proposed aims, allowing the structure to be monitored effectively.

It is therefore clear that numerous variants of the sensor and of the system and method described above can be implemented by a person skilled in the art, without departing from the scope of protection as defined by the attached claims.

For example, in one embodiment, the two sensing areas which constitute one of the electrodes of the piezoelectric sensor can be electrically separated, that is to say that there is no electrical connection 112 as in the example of FIG. 1.

Figure 12:
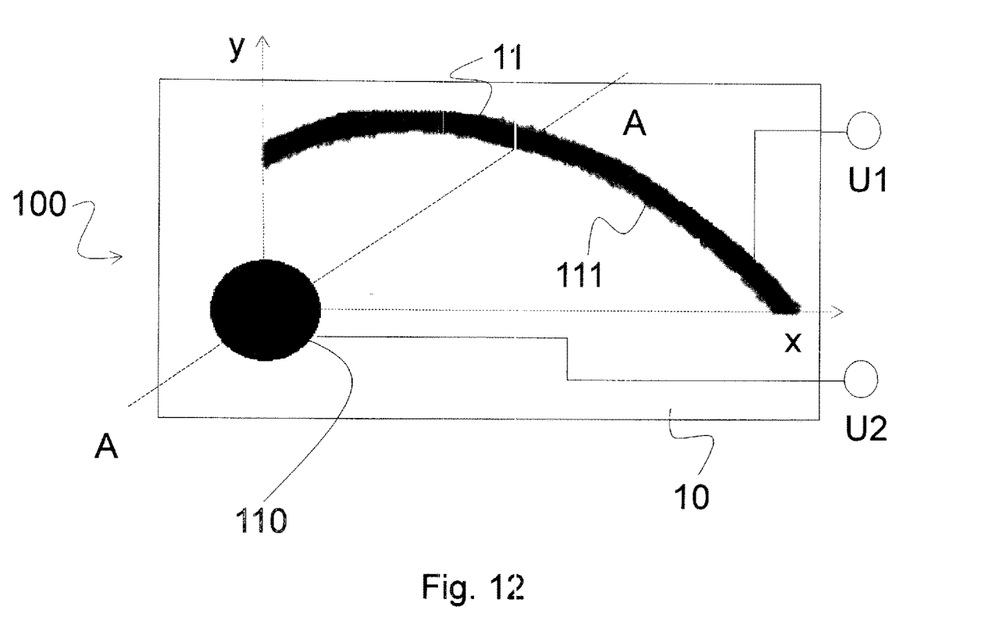
FIG. 12 shows a top view of an alternative piezoelectric sensor to that in FIG. 1, with electrically isolated sensing areas.

In this case, shown in FIG. 12, the piezoelectric sensor 100 includes two sensing areas 110 and 111 which are electrically separated and constitute independent electrodes, to which the common electrode 12 is added. The piezoelectric sensor 100 will thus have two output terminals U1 and U2, at the ends of which there will be two different sensing signals resulting from the same incident elastic wave.

In order to verify the direction of origin and the energy of the wavefront, it is necessary to calculate (in the processing unit 2 or in the central system 901, depending on the embodiment) the cross-correlation between the two signals outputted by the sensor 100. The cross-correlation of these signals has a maximum whose position varies according to changes in the direction of origin of the wavefront, so in order to determine the direction and energy of the wavefront it is necessary to calculate the cross-correlation between these signals and extract the maximum cross-correlation.

The methods for monitoring the integrity of a structure described above with reference to FIGS. 8, 10 and 11 will thus be modified by providing for the calculation of the maximum of the cross-correlation between the pairs of signals generated by the sensor 100 instead of the calculation of the second autocorrelation peak of the signal generated by the sensor 1.

Also the cases of the dispersive and anisotropic propagations will be addressed with solutions similar to those described above for the solution based on the areas not electrically separated, taking care to replace the processing steps based on autocorrelation with those based on the cross-correlation of the pairs of signals collected.

It will therefore be possible to monitor a structure in an anisotropic and dispersive material by means of a piezoelectric sensor in which the two sensing areas of the first electric contact element are mutually electrically isolated, in which the piezoelectric sensor generates a pair of electrical signals upon the detection of an elastic wave, and by including the following steps:

characterizing the structure by identifying, for N different preselected directions within the structure, different dispersion curves for different modes of propagation of an elastic wave in the N preselected directions,     applying N times a compensation algorithm from the dispersion to the pairs of signals generated by the piezoelectric sensor in such a way as to generate N pairs of compensated signals, each time considering the dispersion curves of the more energetic of the modes of propagation of the wave along the preselected direction taken into consideration, calculating N cross-correlation signals of the N pairs of compensated signals, for each of said N calculated cross-correlation signals, extracting the maximum peak of its envelope, from among the N extracted maximum peaks, determining the peak with the greatest amplitude, determining the direction of origin of the elastic wave as a function of the position of the peak of maximum amplitude.

Figure 13:
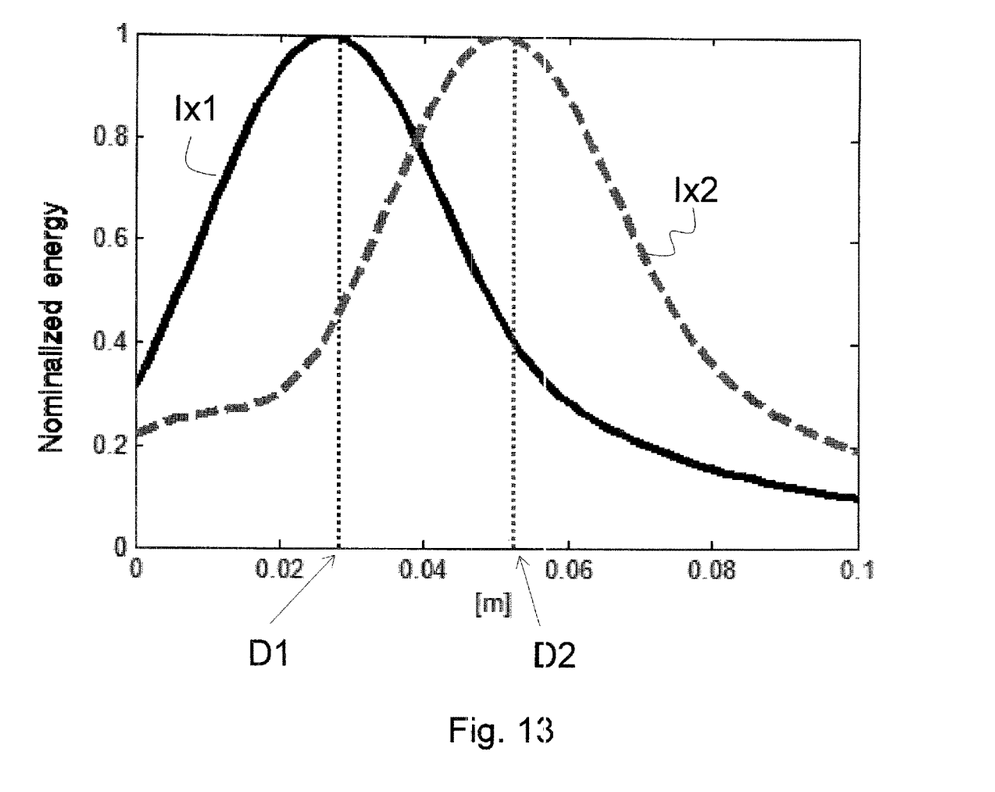
FIG. 13 shows the cross-correlation signals of the signals generated by the sensor in FIG. 12 in response to the waves shown in FIG. 3.

FIG. 13 shows the trend of the cross-correlation envelope (IX1 and IX2) of the two signals generated by the wavefronts F1 and F2 of the type illustrated in FIG. 3. As can be appreciated from FIG. 13, Ix1 and Ix2 both have a main peak whose distance from the origin depends on the point of impact of the wavefront with the sensing area 111.

Although the examples described above have presented a piezoelectric sensor capable of detecting guided waves in a sensing interval of 90°, it is clear that by following the principles explained above piezoelectric sensors with different sensing ranges can be realized.

Although in the embodiments described above the electrode 12 has been described as a conductive layer of constant thickness, this requirement is not essential and the electrode 12 may have other shapes and also be composed of two or more electrically connected parts. In every case, the electrode 12 is preferably disposed on a surface area that is greater than or equal to that occupied by the first contact element 11.

The invention claimed is:

1. Piezoelectric sensor comprising a piezoelectric material interposed between a first and a second electric contact element, where the first electric contact element comprises at least two sensing areas spatially separated along a sensing direction wherein the first of the said at least two sensing areas has the shape of a segment of an Archimedean spiral or of a logarithmic spiral, such that their distance of said separation varies according to the sensing direction considered.

2. Sensor according to claim 1, in which the second of the said at least two sensing areas has a circular shape.

3. Sensor according to claim 1, in which the sensing areas are electrically connected.

4. Sensor according to claim 1, in which the sensing areas are electrically insulated and the first electric contact element comprises two distinct electrodes, each of said distinct electrodes comprising a respective output terminal each one connected to a respective sensing area of the first electric contact element.

5. Sensor node comprising a piezoelectric sensor according to claim 1, and a processing unit designed to digitize an electrical signal generated by the piezoelectric sensor in response to the detection of an elastic wave.

6. Sensor node according to claim 5, wherein the processing unit is adapted to transmit the digitized signal to a remote device.

7. Sensor node according to claim 6, further comprising means for receiving and/ or transmitting data over optical fiber.

8. Sensor node according to claim 6, further comprising a memory for temporarily storing data received on a data input.

9. Sensor node according to claim 5, wherein the processing unit is adapted to calculate the direction of origin and/ or the energy of the elastic wave and to transmit data on the direction of origin and/ or the energy of the elastic wave to a remote device.

10. System for monitoring the integrity of a structure, comprising a plurality of sensor nodes for detecting elastic waves in the monitored structure, a central processing system operatively connected to said sensor nodes and designed to process data transmitted by said sensor nodes, wherein each of said sensor nodes comprises a piezoelectric sensor according to claim 1, and a processing unit designed to digitize an electrical signal generated by the piezoelectric sensor in response to the detection of an elastic wave which is propagated in the structure, said processing unit being also designed to transmit the digitized signal to a remote device.

11. System according to claim 10, wherein said remote device is one between a sensor node of said plurality and the central processing system, wherein the processing unit comprises an input for receiving data transmitted from another sensor node and is designed to retransmit from an output the data received on said input.

12. System according to claim 10, wherein the processing unit is designed to transmit the identifier of the sensor node to which it belongs and temporal information on when the electric signal generated by the piezoelectric sensor was detected, and in which the central system is designed —to receive the digitized signal, the temporal information and the identifier transmitted from each sensor node, —for each sensor node to calculate the direction of origin and/ or the energy of said wave.

13. System according to claim 12, wherein the central system comprises a memory area containing information on the position and shape of said plurality of sensor nodes and is designed to calculate a point of impact and/ or the energy of an object's impact with the structure.

14. System according to claim 10, wherein the sensor nodes are designed to receive and transmit data over optical fiber.

15. Method for distinguishing the direction of origin of a wavefront affecting a piezoelectric sensor for monitoring the integrity of a structure upon which the sensor is applied, within which a wave guided is detected by the piezoelectric sensor along a sensing direction comprising:

detecting the time interval between the time instant when the wavefront impacts point (P111) of a first sensing area (111) of a first electric contact element (11) of the piezoelectric sensor spatially separated from a second sensing area (110) of the first electric contact element (11) of the piezoelectric sensor, said first sensing area (111) having the shape of a segment of an Archimedean spiral or of a logarithmic spiral, and the time instant when the wavefront impacts a point (P110) in the second sensing area (110) of the first electric contact element (11) of the piezoelectric sensor along the sensing direction of the wavefront, said second sensing area (110) having a circular shape, determine the sensing direction of the wavefront affecting the piezoelectric sensor on the basis of the said time interval and the distance between the two impact points (P111, P110) being known the wave velocity and the geometrical shape of the spiral of the first sensing area (111).

16. Method according to claim 15, wherein the method provides for:

electrically connecting each other the two sensing areas of the first electric contact element —calculating the autocorrelation envelope of the signal generated by the piezoelectric sensor or by a signal derived from the one generated by the piezoelectric sensor when it is affected by the wavefront, extracting the second peak of the autocorrelation signal, determining the direction of origin of the guided wave on the basis of the position of the second peak of the autocorrelation signal.

17. Method according to claim 15, wherein the method involves:

electrically connecting each other the two sensing areas of the first electric contact element compensating the signal generated by the piezoelectric sensor upon detection of a guided elastic wave within the structure for any dispersion suffered by the elastic wave, calculating the autocorrelation envelope of the compensated signal, extracting the second peak of the autocorrelation signal, determining the direction of origin of the guided wave on the basis of the position of the second peak of the autocorrelation signal.

18. Method according to claim 17, wherein in the event of a multimodal propagation of the elastic wave within the structure the compensation of the signal is effected using the dispersion curves of the most energetic method.

19. Method according to claim 15, when the structure consists of an anisotropic and dispersive material, said structure within which the wavefront is guided and detected by the piezoelectric sensor, the method involves:

electrically connecting each other the two sensing areas of the first electric contact element characterizing the structure by detecting, for N different preselected directions within the structure, different dispersion curves for different propagation modes of an elastic wave in the N different preselected directions, applying N times an algorithm to compensate the dispersion of the signal generated by the piezoelectric sensor in such a way as to generate N compensated signals, each time considering the dispersion curves for the most energetic of the propagation modes of the wave along the preselected direction taken into consideration,—calculating the autocorrelation signal of the N compensated signals,—for each of the N calculated autocorrelation signals, extracting the second peak of the envelope of said autocorrelation signals, among the extracted second peaks, determining the one of maximum amplitude, determining the direction of origin of the guided wave on the basis of the position of the second peak of maximum amplitude.

20. Method according to claim 15, wherein the method involves:

calculating the cross-correlation envelope of the two signals generated by the piezoelectric sensor when a guided wave within the structure arrives on the two sensing areas, being the two sensing areas electrically isolated from one another and constituting separate electrodes, extracting the maximum peak of the cross-correlation envelope, determining the direction of origin of the guided wave on the basis of the position of the maximum peak of the cross-correlation envelope.

21. Method according to claim 15, wherein the method involves:

compensating the two signals generated by the piezoelectric sensor upon detection of a guided elastic wave within the structure for any dispersion suffered by the elastic wave, said two signals generated by the two sensing areas when affected by the wavefront, being the two sensing areas electrically isolated from one another and constituting separate electrodes, calculating the autocorrelation envelope of the two compensated signals, —extracting the maximum peak of the autocorrelation signal, —determining the direction of origin of the guided wave on the basis of the position of the maximum peak of the autocorrelation signal.

22. Method according to claim 21, wherein in the event of a multimodal propagation of the elastic wave within the structure the compensation of the two signals is effected using the dispersion curves of the most energetic method.

23. Method according to claim 15, wherein the piezoelectric sensor generates a pair of electric signals upon detection of an elastic wave being the two sensing areas electrically isolated from one another and constituting separate electrodes, wherein in the event the structure consists of an anisotropic and dispersive material, the method involves:

characterizing the structure by determining, for N different preselected directions within the structure, different dispersion curves for different propagation modes of an elastic wave in the N different preselected directions, applying N times an algorithm to compensate the dispersion of the pair of signals generated by the piezoelectric sensor in such a way as to generate N pairs of compensated signals, each time considering the dispersion curves for the most energetic of the propagation modes of the wave along the preselected direction taken into consideration, calculating N cross-correlation signals of the N pairs of compensated signals, —for each of the N calculated cross-correlation signals, extracting the maximum peak of the relevant envelope, among the N maximum peaks extracted, determining the one of maximum amplitude, determining the direction of origin of the elastic wave on the basis of the position of the peak of maximum amplitude.

* * * * *